US008455023B2

United States Patent
Wang et al.

(10) Patent No.: US 8,455,023 B2
(45) Date of Patent: Jun. 4, 2013

(54) COMPOSITION FOR INHIBITING MELANOGENESIS AND USE THEREOF

(75) Inventors: Hui-Min Wang, Kaohsiung (TW); Chung-Yi Chen, Kaohsiung (TW); Zhi-Hong Wen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 126 days.

(21) Appl. No.: 12/848,380

(22) Filed: Aug. 2, 2010

(65) Prior Publication Data

US 2011/0212194 A1   Sep. 1, 2011

(30) Foreign Application Priority Data

Feb. 26, 2010 (TW) ................................ 99105580 A

(51) Int. Cl.
*A61K 36/54* (2006.01)

(52) U.S. Cl.
USPC .......................................................... 424/739

(58) Field of Classification Search
None
See application file for complete search history.

(56) References Cited

PUBLICATIONS

Lin et al. Bioactivity Investigation of Lauraceae Trees Grown in Taiwan. Pharmaceutical Biology. 2007 vol. 45, No. 8, pp. 638-644.*
Reader's Digest. The Healing Power of Vitamins, Minerals, and Herbs. Jan. 11, 1999. pp. 23-24.*

* cited by examiner

*Primary Examiner* — Amy L Clark
(74) *Attorney, Agent, or Firm* — WPAT, P.C.; Anthony King

(57) ABSTRACT

The present invention provides a *Cinnamomum subavenium* extract for inhibiting melanogenesis. The present invention also provides a composition for inhibiting melanogenesis including compounds inhibit tyrosinase activity.

4 Claims, 5 Drawing Sheets

COMPOSITION FOR INHIBITING MELANOGENESIS AND USE THEREOF

FIELD OF THE INVENTION

The present invention is related to a *Cinnamomum subavenium* extract and use therefore. The *Cinnamomum subavenium* extract can be applied in whitening cosmetology by inhibiting melanogenesis.

BACKGROUND OF THE INVENTION

Skin melanin is produced by melanocytes which locate in stratum of epidermis. Human skin usually have similar level of melanocytes, however, different population may have variation of melanin gene expression. Melanin is an insoluble high molecular weight polymer with compact molecular structure, which binds to protein very often. Based on its structure, melanin can be grouped into eumelanins, pheomelanins and allomelanins. Melanin in mammals is a mixed population of eumelanins and pheomelanins in various ratios. The quantities and types of these two kinds of melanin are controlled by 4 to 6 genes through incomplete dominant inheritance. Each gene copy is derived from both parents who express different skin colors after combination.

Melanin synthesis requires several enzymes and molecules for biochemical reactions, such as tyrosine, tyrosinase and oxygen. Tyrosinase oxidizes tyrosine into dihydroxyphenylalanine, transforms it to dopachrome, indoles, and finally melanin (Wulf, et al. Skin aging and natural photoprotection. 2004 Micron, 35, 185-191). Rate limiting step of that reaction is the step that the catalyzing by tyrosinase from dihydroxyphenylalanine into dopachrome. Auto-oxidation of dopachrome produces melanin. Tyrosinase is a copper containing metal enzyme, which is synthesized by melanocytes. Tyrosinase plays a very important role of melanin production. When tyrosinase activity increases, melanin production increases. On the contrary, when tyrosinase activity is inhibited, the ability of melanocyte producing melanin drops accordingly.

There are many reasons cause melanin precipitation. The elevation of tyrosinase activity leads to melanin synthesis when skin is exposed to UV radiation. Copper concentration elevation in blood also increases tyrosinase activity. Therefore, inhibition of tyrosinase activity is one way to reduce melanin synthesis.

The mechanism of melanin formation inhibition can be grouped into four categories: 1. reducing tyrosinase activity to inhibit melanin synthesis such as tyrosinase inhibitor; 2. minimizing melanocyte function with cytotoxic material to reduce melanocyte proliferation or make it unable to produce melanin; 3. reducing or preventing dihydroxyphenylalanine auto-oxidation such as anti-oxidant; and 4. inhibiting skin inflammation such as inflammatory swelling reaction after sun exposure. Therefore, for skin whitening cosmetology usage, one can block UV, remove free radicals, inhibit tyrosinase synthesis, inhibit tyrosinase activity and block melanin synthesis or fasten its metabolism and etc.

More patents have been found as tyrosinase inhibitors based on the first mechanism. Brief description is shown below. U.S. Pat. No. 5,723,109 used salicylic acid derivative as tyrosinase inhibitor, and U.S. Pat. No. 5,730,962 revealed a synthetic benzofuran and its derivatives for tyrosinase inhibition.

Several natural plant or food extracts also have tyrosinase inhibition effects. U.S. Pat. No. 5,824,320 reveals an extract and its derivatives from Aphloia and Mangifera leaf, which inhibits tyrosinase and collagenase activity. U.S. Pat. No. 5,968,487 provides a synthetic 5-hydroxy-4-oxo-4H-pyran-2-ylmethyl 2-oxothiazolidine-4-carboxylate to inhibit human melanin synthesis as skin whitening agent. U.S. Pat. No. 6,750,229 provides a soybean extracted STI and Bowman-Birk protease inhibitor, which Bowman-Birk protease inhibitor functions on upper epidermis showing significant melanin inhibition along with increasing concentration. The melanin inhibition reaches more than 40% when combining these two extracts on pigs.

As described above, there are several pharmaceuticals can be used for whitening cosmetic agents. However, applying these whitening cosmetic ingredients alone shows weak effect. The product stability or safety issues such as skin irritation are not satisfactory for market demand. For example, it is known that ascorbic acid is not stable and easy to induce dermatitis. Kojic Acid and its derivatives have strong whitening effect but are easy to degrade under light or heat exposure. Hydroquinone has strong whitening effect but low stability. It also has discoloring issues during cosmetic production such as micelle and lotion as well as issues of inducing allergic contact dermatitis. Regarding biophamaceuticals such as GuangDong Ginseng, it is too pricey to generate low cost whitening agent for regular consumers.

In summary, there are still demands on compositions with excellent whitening effect at low dose or compositions with good safety and stability without skin irritation, and compositions easy to take or combine with food, cosmetics, and pharmaceuticals.

BRIEF DESCRIPTION OF THE DRAWINGS

FIG. 2 shows the results of different concentrations of linderanolide B and subamolide A on human melanocyte. Kojic acid, N-phenylthiourea and MSH are also included.

SUMMARY OF THE INVENTION

Figure 1:
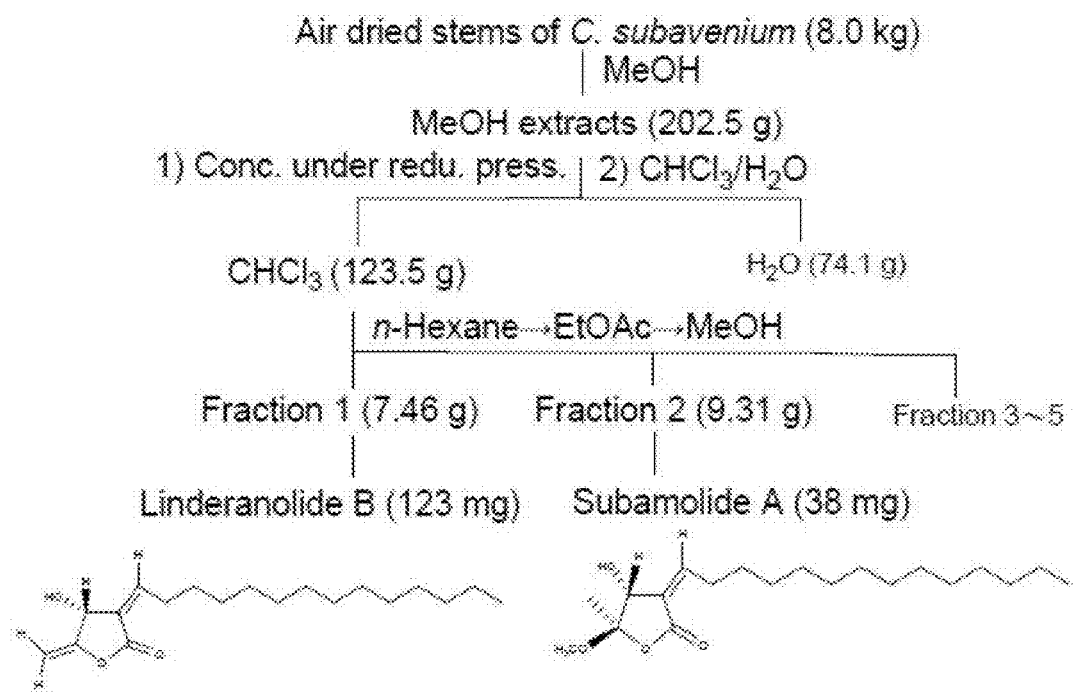
FIG. 1 shows the flow chart of extraction and purification of two compounds—linderanolide B and subamolide A.

The present invention provides a composition for inhibiting melanogenesis, which comprises two extracts isolated from the stems of *Cinnamomum subavenium*—linderanolide B and subamolide A. These two components contain anti-tyrosinase ability, so as to inhibit melanogenesis in cells or subjects and to be applied in whitening cosmetology.

DETAILED DESCRIPTION OF THE INVENTION

The present invention includes a *Cinnamomum subavenium* extract which is obtained from the following steps: extracting stems of *Cinnamomum subavenium* by organic solvent; adding product from previous step into water as suspension; adding chloroform solution to the suspension to generate layers; separating chloroform layer from others;

applying chloroform layer to column liquid chromatography and eluting said extract with an alkane and ester mixture. The alkane of the present invention includes n-hexane and the ester of the present invention includes ethyl acetate.

The *Cinnamomum subavenium* extract of the present invention can be added into drinks, cosmetics or pharmaceutical products. The drinks include juices, tea, noodles, diary products or seasoning, said cosmetics include toner, gel, cleansing reagent, ointment, paste, lotion, liquid or cream foundation, lip sticks, powder, cleansing gel, hair spray and cosmetics in liquid, solid, gel forms made by other known methods for cosmetics manufacture; said pharmaceutical products include powder, capsule, spray, gel, ointment, flake, suppository, powder drink, patch, pill, tablet, injection, infusion solution, suspension, intravenous emulsion, slow releasing agent, controlled releasing agent or forms made by other known methods for pharmaceutical manufacture.

The present invention also provides a use of pharmaceutical product which is prepared with an extract of said extract for melanogenesis inhibition, wherein said pharmaceutical product inhibits individual's tyrosinase activity to reduce melanin synthesis and the active ingredient of said pharmaceutical product includes following compounds of chemical structure I or II as shown below,

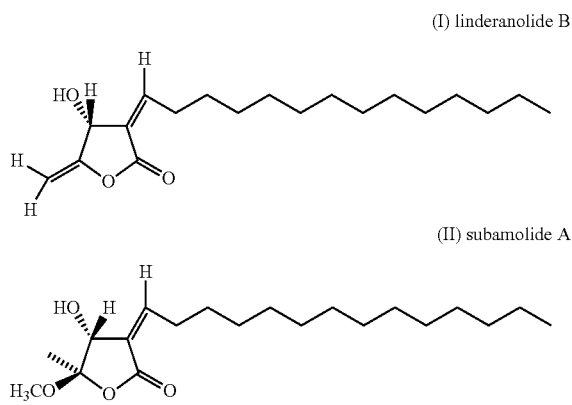

and its salt, ester or solvate. The individual includes animals or human.

The present invention also provides a composition for inhibiting melanogenesis including compounds of chemical structure I or II as shown below,

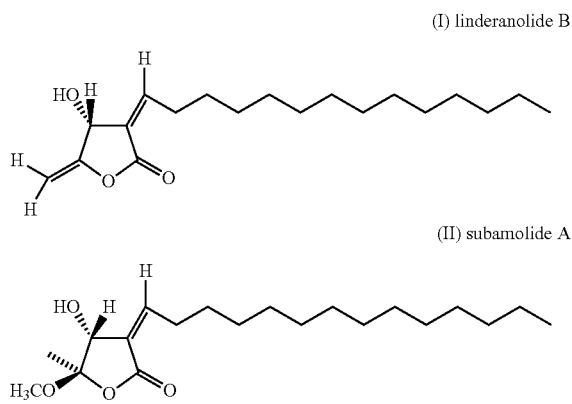

and its salt, ester or solvate.

The solvate indicates that solvent molecule may be incorporated into the compound lattice during crystallization forming a solvate of said compound.

Both compounds have tyrosine kinase inhibition activity.

The composition or extract of the present invention can be added into drinks, cosmetics or pharmaceuticals. For example, drinks include sports drink, carbonated drink, soft drinks containing juice or black tea; snacks include cake, cookie, bread, soft candy or ice cream; noodles includes udon, noodle, ramen, floury food; others include miso, soy sauce, vinegar, vegetable oil, sesame oil, butter, cheese, soy milk or milk and etc. These can be taken as food or drinks no matter the types or morphology. The whitening ingredient of the present invention is dissolved and mixed with drinks to produce these products.

For example, cosmetics include toner, gel, cleansing reagent, ointment, paste, lotion, liquid or cream foundation, lip sticks, powder, cleansing gel, hair spray and liquid, solid, gel and paste material for external use, and soft capsules or oral spray. Besides the whitening cosmetic ingredient of the present invention, other materials can be used through known method for manufacture. Commonly used other materials include lipids (such as bees wax and carnauba wax, jojoba oil, mink oil, cocoa butter, coconut oil, palm oil, camellia oil, sesame oil, castor oil, olive oil and etc.), surfactants (such as glycerin fatty acid ester, polyoxyethylene sorbitan fatty acid ester, polyoxyethylene alkyl ether, polyoxyethylene ceteth, sorbitan fatty acid ester, polyoxyethylene hydrogenated castor oil, polyglycerol fatty acid ester and etc.), low or high alcohols (such as cetyl alcohol, isostearic alcohol, lauryl alcohol, cetyl alcohol, behenyl alcohol, octyldodecanol and etc.), fatty acids (such as lauric acid, myristic acid, palmitic acid, stearic acid, undecylenic acid, oleic acid and etc.), water soluble polymers (such as carboxyvinyl polymer, alkyl modified carboxyl polymer, cellulose, Ca-alginate and etc.), polysaccharides (such as hyaluronan, chondroitin sulfate and etc.), peptides (such collagen and etc.), preservatives (such as benzoic acid and its salt derivatives, isopropyl methylphenol, chlorohexidine, o-phenylphenol, chlorhexidine gluconate, 4-Chloro-2-methylphenol, chlorphenesin, chlorobutanol, sorbic acid and its salt derivatives, dehydroacetic acid and its salt derivatives, paraoxy ethylene benzoate ester, 3-trifluoromethyl-4,4-dichloro carbanilide and etc.), thickening agents (such as sodium carboxymethyl cellulose, Ca-alginate, polysaccharide and etc.), humercants (such as glycerol, xylitol, sorbitol, dipropylene glycol, butanediol, propylene glycol, polyethylene glycols 200-600, polyoxyethylene methyl glycoside, maltitol, mannitol and etc.), pigments, spices, water or pH conditioner and etc.

Pharmaceuticals include spread, sticker, ointment, gelatin spread for external use, and granule, fine granule, tablet, capsule, syrup or liquid and etc. for oral intake. Besides whitening cosmetic ingredient of the present invention, other materials can be used through known method for manufacture. Commonly used other materials include all kinds of supplements such as excipients (such as lactose, sugar, glucose, starch, crystalline cellulose and etc.), adhesives (such as starch paste, hydroxypropyl cellulose solution, carboxymethylcellulose solution, arabic gum solution, gelatin solution, sodium alginate solution and etc.), disintegrants (such as starch, sodium carboxymethyl cellulose, calcium carbonate and etc.), lubricants (such as magnesium stearate, pencil stone, stearic acid, Calcium octadecanoate and etc.), surfactants (such as polysorbate 80, polyoxyethylene hydrogenated castor oil and etc.) or thickeners (such as hydroxyethyl cellulose, hydroxypropyl cellulose, polyvinyl alcohol, polyethylene glycols and etc.). Formulation of oral pharmaceuticals includes chewing gum or Lozenges and etc.

EXAMPLES

The examples below are non-limiting and are merely representative of various aspects and features of the present invention.

The present invention applies *Cinnamomum subavenium* extract to inhibit melanin biosynthesis. It utilizes cell assay and zebrafish in viva assay to demonstrate that said extract has anti-tyrosinase activity to reduce melanin expression. The following figures and description are used as a reference of the best embodiments of the present invention but not the limitation of the scope of the present invention.

Example 1

Experimental Materials

*Cinnamomum subavenium* belongs to *Cinnamomum* genus, which is one of Taiwanese native evergreen trees located in 500-1500 meters. The bark has cinnamon smell which can be used for spices. The extracted leaf oil can be used as food, cigarette spices or anti-bacterial agents.

Example 2

Extraction and Purification

Two compounds, linderanolide B and subamolide A, were extracted from the stem of *Cinnamomum subavenium*, which were referred as compound (I) and (II) below.

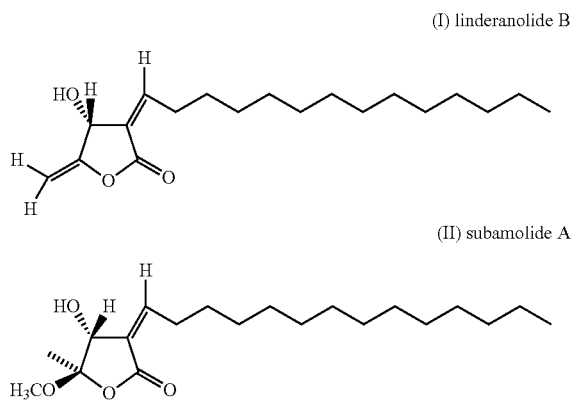

Eight kg of air dried *Cinnamomum subavenium* stems was extracted with 80 L of methanol for 6 times to harvest total 202.5 g of extract via room temperature reduced pressure condition. The extract was resuspended in 1 L of water. Two L of chloroform (CHCl3) was added in 5 aliquots to separate the solution. Extract dissolved in chloroform layer was 123.5 g and dissolved in water layer was 74.1 g. Chloroform extract of 123.5 g was applied to silica gel (800 g, 70-230 (mesh)) chromatography. N-hexane, EtOAc and methanol were mixed as elution solution to separate 5 fractions of eluates.

Part of the eluate from fraction 1 (7.46 g; group 1/tube 1 shown as 1-1) was eluted with hexane-ethyl acetate (30:1), and then partitioned with enough ethyl acetate to get 10 tubes of eluates (1-1~1-10). Group 1/tube 3 (4.02 g) was eluted with hexane-ethyl acetate (40:1), and ethyl acetate was added continuously to get 3 tubes of eluates (1-3-1~1-3-3). Eluate of tube 1-3-2 weighted 4.11 g was applied to hexane-ethyl acetate (40:1) elution, silica gel column chromatography and thin layer chromatography (hexane-ethyl acetate (30:1)). The final chromatography result of group 1 ended with 2.31 g of isolinderanolide B and 134 mg of linderanolide B.

The fraction 2 eluate (9.31 g) was applied to silica gel chromatography and eluted with hexane-ethyl acetate (10:1). Ethyl acetate was added continuously to get 3 tubes of eluates (2-1~2-5). Eluate of tube 2-4 weighted 1.31 g was applied to silica gel chromatography and eluted with hexane-acetate (40:1). Ethyl acetate was added continuously to get 4 tubes of eluates (2-4-1~2-4-4). Eluate of tube 2-4-2 (1.06 g) was further eluted with hexane-ethyl acetate (10:1), applied to silica gel column chromatography and thin layer chromatography (hexane-ethyl acetate (30:1)) for final separation of subamolide A (38 mg).

Example 3

Cell Assay

This embodiment used human melanocytes to test tyrosinase inhibition effects of compound (I) and compound (II).

Cell Culture

Neonatal foreskin primary human epidermal melanocytes (HEMn-MP) was purchased from Cascade Biologics™, and cultured in 254 medium (Cascade Biologics™) with human melanocyte growth supplement (HMGS, cat. #S-002-5). Cells were maintained at 37° C. humid environment (5% $CO_2$). Neonatal foreskin primary human epidermal melanocytes (HEMn-MP) were cultured in 24-Well plates at seeding density of $10^5$ cells/well.

Toxicity Assay

Different concentrations of compound (I) and (II) (0.01 μM, 0.1 μM, 1 μM, 5 μM, 10 μM) and 100 μM kojic acid, 100 μM N-phenylthiourea (PTU) and 0.1 μM a-Melanocyte-Stimulating Hormone (MSH) were added into cell culture dish. MTS assay (Mosmann T, Rapid colorimetric assay for cellular growth and survival: application to proliferation and cytotoxicity assays J Immunol Methods 1983 16; 65(1-2):55-63) was used for cell toxicity assay. Kojic acid and N-phenylthiourea are known melanin inhibitors. The stimulation of MSH to melanin synthesis was used as a reference for comparison of compound (I) and (II). Experimental results were shown in Table 1 and FIG. 2A. Control group value was set as 100% which obtained from 3 independent experiments.

TABLE 1

| Cell activity | | | |
|---|---|---|---|
| Test materials | | Cell activity percentage (%) | SD (n ≧ 3) |
| Control group | | 100 | 9.866606 |
| Linderanolide B | 0.01 μM | 94.18605 | 11.51104 |
| | 0.1 μM | 87.51938 | 4.385158 |
| | 1 μM | 83 | 6.029593 |
| | 5 μM | 62.40741 | 1.386484 |
| | 10 μM | 54.25926 | 1.386484 |
| Subamolide A | 0.01 μM | 93.41085 | 4.933303 |
| | 0.1 μM | 85.65891 | 3.837014 |
| | 1 μM | 73.91473 | 6.577737 |
| | 5 μM | 54.68712 | 9.410774 |
| | 10 μM | 44.91043 | 0.924323 |
| MSH | | 107.7519 | 2.192579 |
| N-phenylthiourea | | 79.06977 | 0.67 |
| Kojic acid | | 72.86822 | 5.481448 |

Figure 2A:
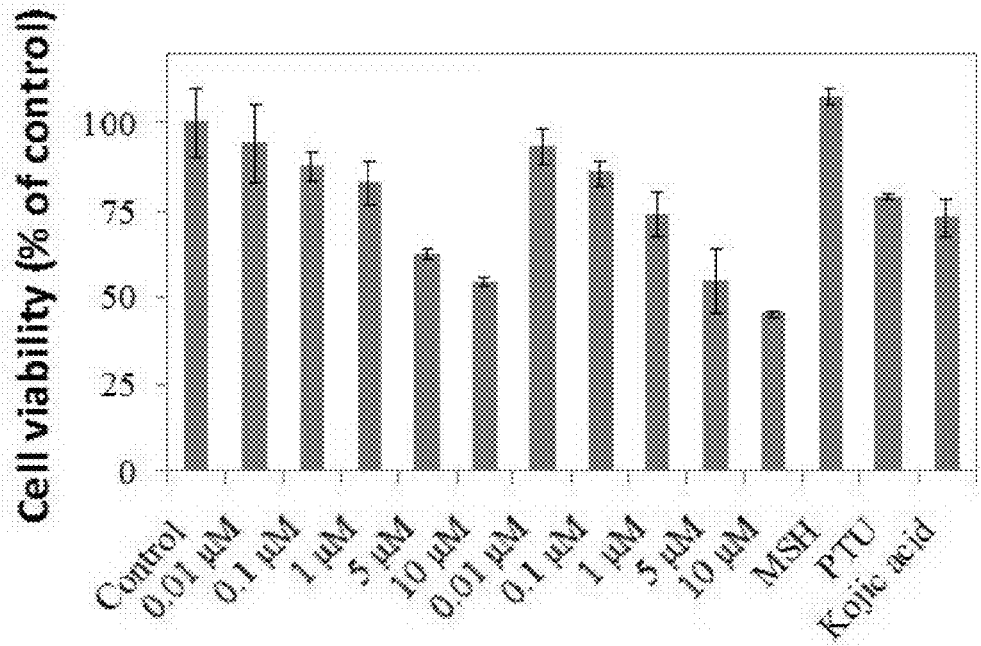
FIG. 2A shows cell toxicity result.

As shown in FIG. 2A, the control group value was set as 100%. Cell activity was reduced along with higher concentrations of compound (I) and (II). N-phenylthiourea and kojic acid had less effects on cell activity.

Tyrosinase Activity Assay

Based on Yoshimura's method (Yoshimura et al., Effects of all-trans retinoic acid on melanogenesis in pigmented skin equivalents and monolayer culture of melanocytes 2001 J. Dermatol. Sci. 27 Suppl 1, S68-75), dopachrome biosynthesis rate was used to determine tyrosinase activity. HEMn-MP cells (105 cells/well) were cultured in 24-well plates and 500 µl of DMEM (Dulbecco's modified Eagle's medium) was added into each well as well as testing compound (I), (II) or kojic acid, N-phenylthiourea and MSH for 3 days.

Cultured cells were rinsed with Fetal Bovine Serum (FBS) resuspend in 1% Triton X-100/PBS. Cell lysate was harvested. L-Dopa and L-tyrosine 10 µl (10 mM in 0.1M PBS, pH 6.8) were added and incubated at 37° C. for 3 hours. After reaction, the OD 490 nm value was measured. The results were shown in Table 2 and FIG. 2B. Control group value was set as 100%, and all results were obtained from 3 independent experiments.

Figure 2B:
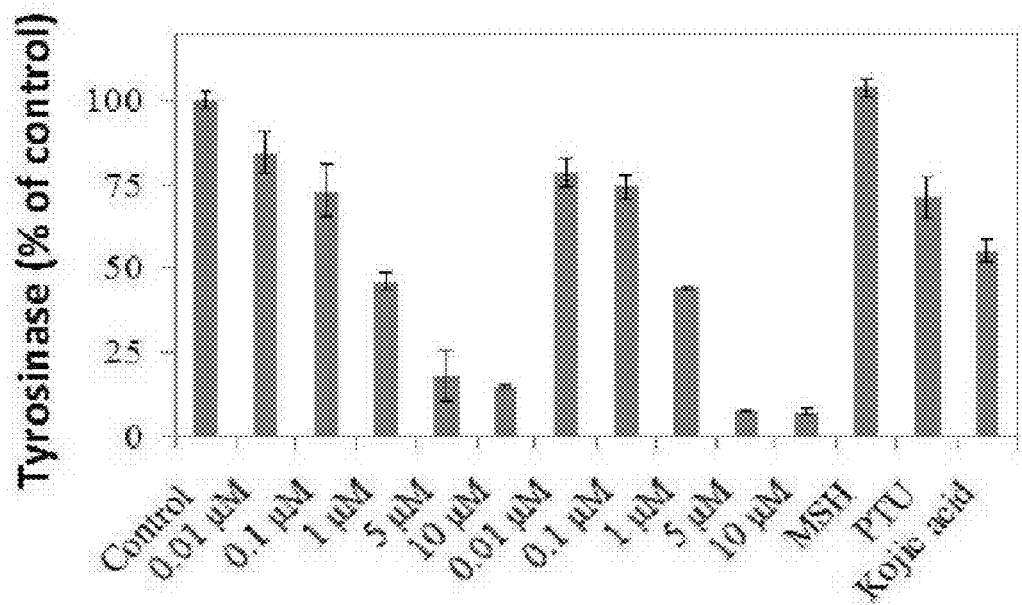
FIG. 2B shows tyrosinase activity results.

As shown in FIG. 2B, tyrosinase activity was reduced along with elevated concentrations of compound (I) and (II). N-phenylthiourea and kojic acid were less effective to tyrosinase activity.

TABLE 2

Tyrosinase activity

| Test materials | | Tyrosinase activity percentage (%) | SD (n ≧ 3) |
|---|---|---|---|
| Control group | | 100 | 2.668327 |
| Linderanolide B | 0.01 µM | 84.15094 | 6.009965 |
| | 0.1 µM | 72.95597 | 7.78885 |
| | 1 µM | 45.91195 | 2.668327 |
| | 5 µM | 18.03684 | 7.65657 |
| | 10 µM | 14.59344 | 0.67558 |
| Subamolide A | 0.01 µM | 78.61635 | 4.447212 |
| | 0.1 µM | 74.21384 | 3.55777 |
| | 1 µM | 44.02516 | 0.67 |
| | 5 µM | 7.369018 | 0.450386 |
| | 10 µM | 7.274543 | 1.125966 |
| MSH | | 103.7736 | 2.668327 |
| N-phenylthiourea | | 71.06918 | 6.226097 |
| Kojic acid | | 55.34591 | 3.55777 |

Melanin Quantitation Analysis

Figure 2C:
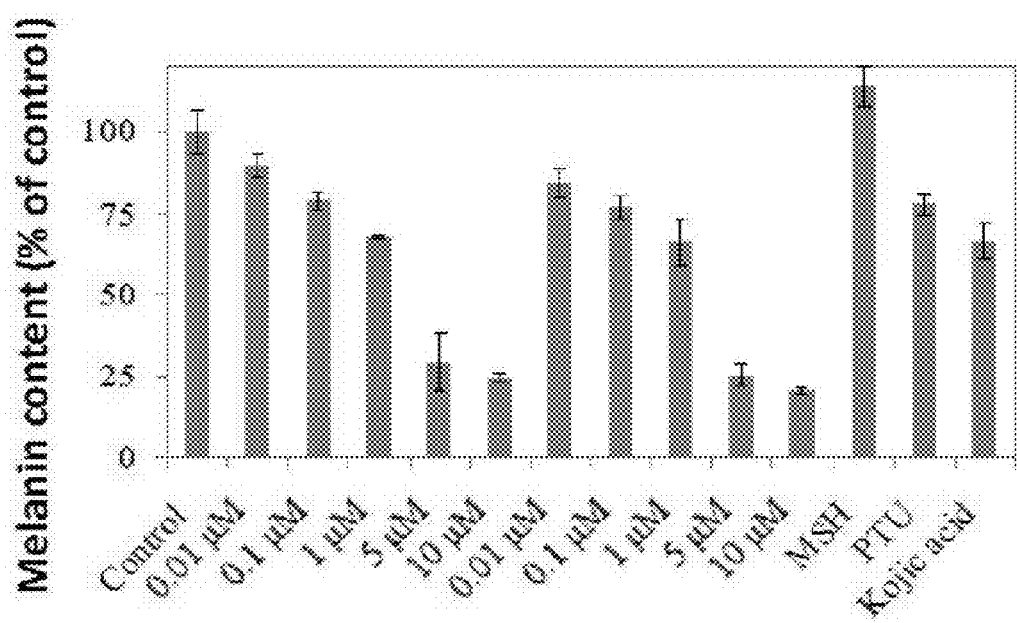
FIG. 2C shows percentage of human melanin content. Control group value is set as 100%.

Lin's method was used to quantify melanin (Lin et al., Constituents from the Formosan apple reduce tyrosinase activity in human epidermal melanocytes 2007 Phytochemistry Volume 68, Issue 8, Pages 1189-1199). Cells were resuspend in 1N NaOH and dimethyl sulfoxide (DSMO), heated at 80° C. for 1 hour, centrifuged for 10 min at 10,000 rpm, and measured OD 405 nm value of supernatant. As shown in Table 3 and FIG. 2C, the control group value was set as 100%. All results obtained from 3 independent experiments. With higher concentrations of compound (I) and (II), cell melanin content decreased. Kojic acid and N-phenylthiourea reduced melanin content and MSH increased melanin content.

TABLE 3

Cell melanin concentration

| Test materials | | Percentage of cellular melanin concentration (%) | SD (n ≧ 3) |
|---|---|---|---|
| Control group | | 100 | 6.898603 |
| Linderanolide B | 0.01 µM | 89.63014 | 3.55777 |
| | 0.1 µM | 78.63014 | 2.668327 |
| | 1 µM | 67.56098 | 0.450386 |
| | 5 µM | 28.92683 | 8.797205 |
| | 10 µM | 24.39024 | 1.724651 |
| Subamolide A | 0.01 µM | 84.10959 | 4.447212 |
| | 0.1 µM | 76.84932 | 3.55777 |
| | 1 µM | 66.09756 | 7.072555 |
| | 5 µM | 25.12195 | 3.449301 |
| | 10 µM | 20.2439 | 1.125966 |
| MSH | | 113.6585 | 5.623253 |
| N-phenylthiourea | | 77.56098 | 3.449301 |
| Kojic acid | | 66.34146 | 5.173952 |

Figure 3:
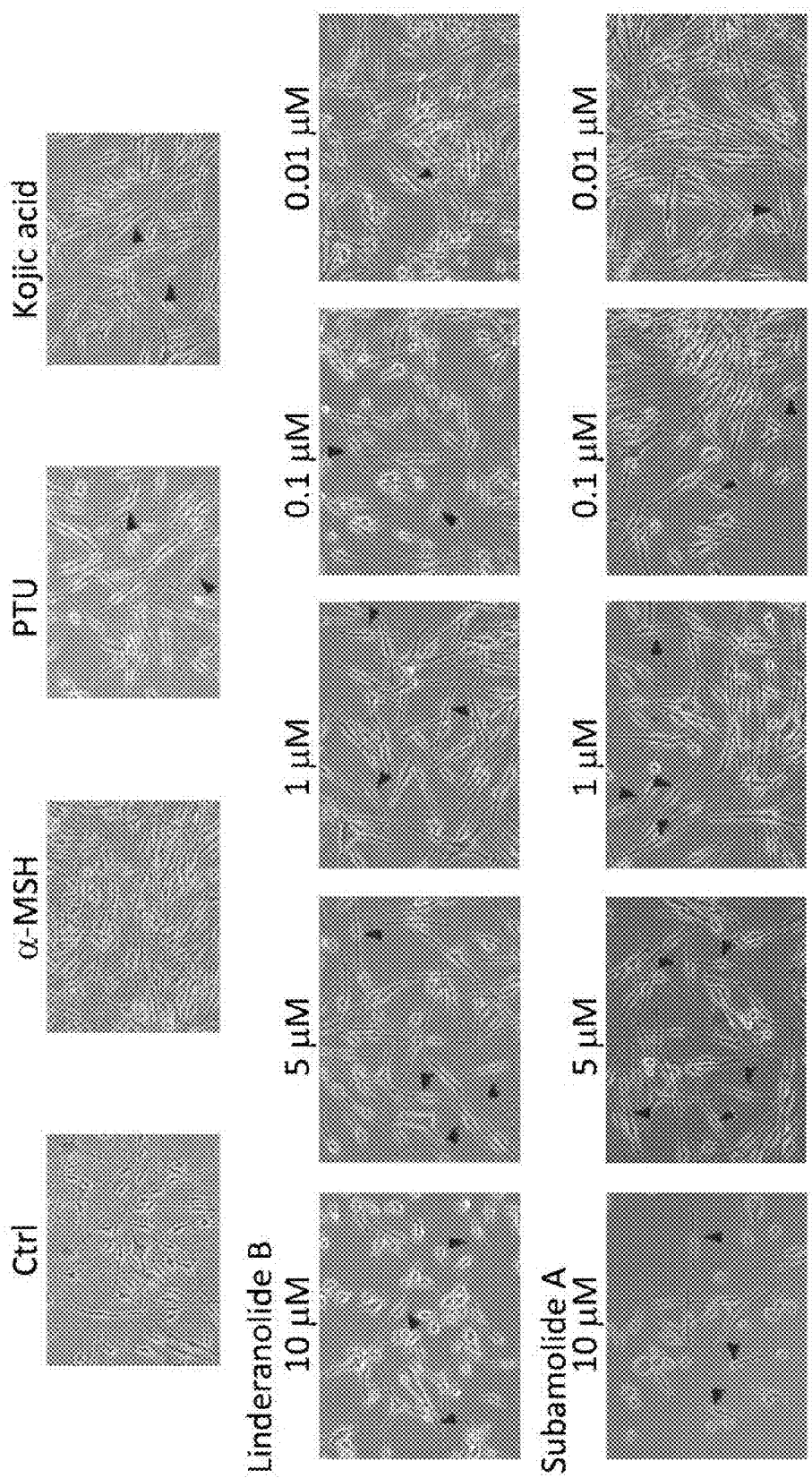
FIG. 3 shows the effect of different concentrations of linderanolide B and subamolide A on cell growth. Microscopic images were taken under 200× magnification bright field view. The arrow head indicates bipolar appearance of neonatal foreskin primary human epidermal melanocyte (HEMn-MP).

FIG. 3 showed the effect of different concentrations of linderanolide B and subamolide A on HEMn-MP cell growth. Under 200× bright field microscope, the control group and low concentration compound (I) and (II) treated cells (FIGS. 3A, 3H, 3I, 3M and 3N) were lined up tightly showing bipolar appearance. Cells treated with α-MSH (FIG. 3B) showed similar appearance.

Cells treated with N-phenylthiourea, kojic acid and higher concentrations of compound (I) and (II) were lined up less regularly. Some cells did not have bipolar characteristics, indicating that the cell structure was destroyed (FIGS. 3C, 3D, 3F, 3G, 3K and 3L). Under high concentrations of compound (I) and (II) treatment, cells were irregular with some appearance variation, indicating that the compounds had partial toxicity to cells (FIGS. 3E and 3J).

Example 4

Zebrafish Animal Experiment

Figure 4:
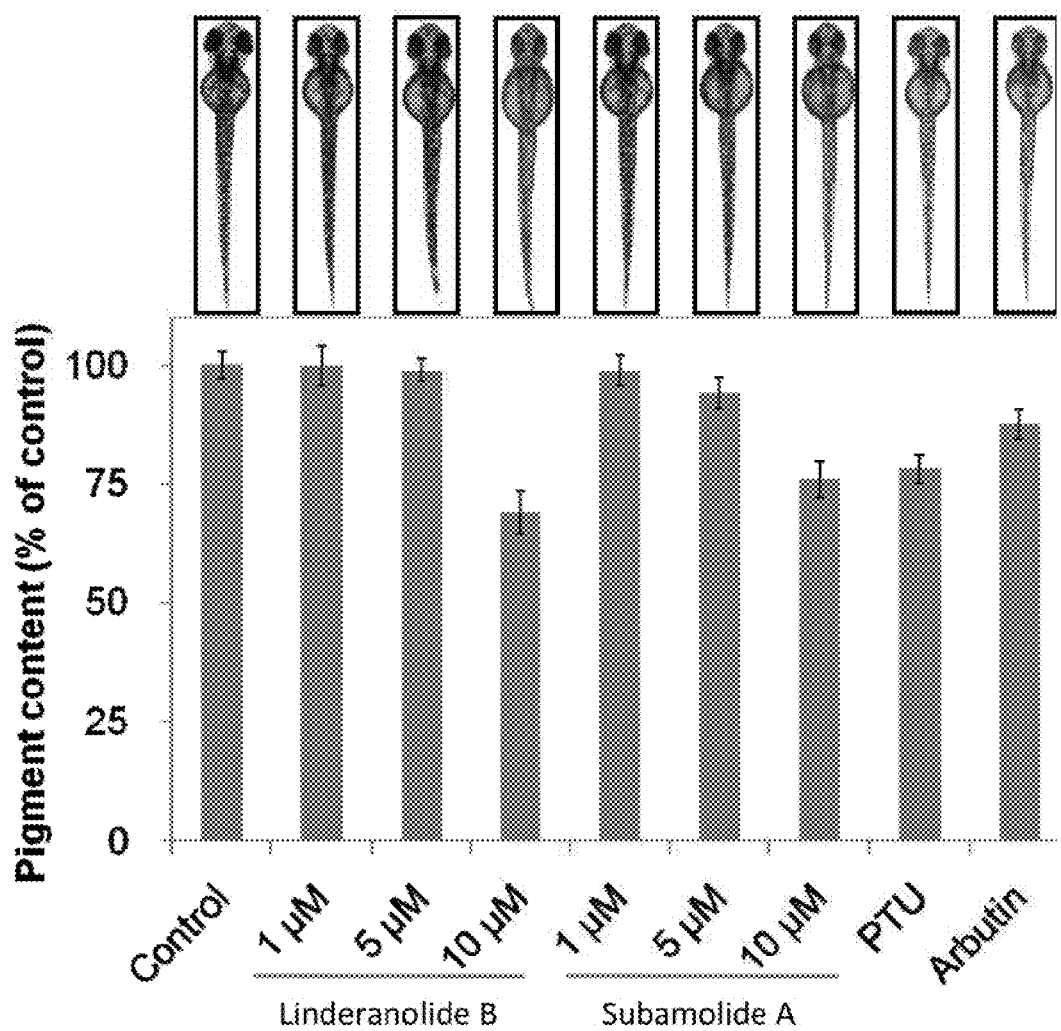
FIG. 4 shows the effect of different concentrations of linderanolide B and subamolide A on zebrafish pigment content. It also includes test results of N-phenylthiourea and arbutin. Control group value is set as 100%.

This embodiment used zebrafish in vivo assay to test the whitening cosmetic effect of two compounds and to test the dosage which causes danger or death of the zebrafish. Different concentrations of two compounds (1 µM, 5 µM, 10 µM), 10 µM N-phenylthiourea and 50 µM arbutin were added into zebrafish embryo culture. Each experiment included 4-9 embryos. As shown in FIG. 4, 10 µM of two compounds reduced 20%~30% of zebrafish pigment, and these were not toxic to zebrafish. However, the effects were less than N-phenylthiourea and arbutin at higher concentrations.

The present invention can be applied to cosmetology, biomedical industry and etc. The main purpose of this invention is used against excessive global UV light stimulating skin melanin biosynthesis along with higher rate of skin cancer. The present invention has confirmed that the extracted compounds can inhibit tyrosinase activity and have great inhibition effect on melanin biosynthesis using normal human skin as research platform.

What is claimed is:

1. A method for whitening skin in a subject in need of skin whitening comprising administering to said subject a composition comprising a therapeutically effective amount of an isolated compound, wherein said isolated compound is

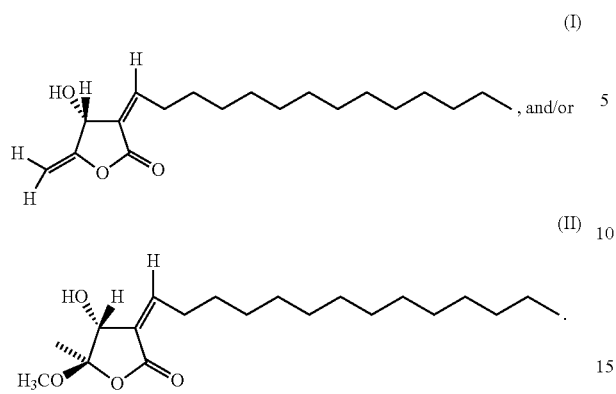

2. The method of claim 1 wherein said composition inhibits tyrosinase activity.

3. The method of claim 1, wherein said composition is in the form of: drinks, cosmetics or pharmaceutical products.

4. The method of claim 1, wherein said composition is in the form of: juices, tea, noodles, dairy products, seasoning, a toner, a gel, a cleaning reagent, an ointment, a paste, a lotion, a liquid or cream foundation, a lip stick, a powder, a cleansing gel, a hair spray, liquid, solid or gel cosmetics, a powder, a capsule, a spray, a flake, a suppository, a powdered drink, a patch, a pill, a tablet, an injection, an infusion solution, a suspension, an intravenous emulsion, a slow release agent or a controlled release agent.

* * * * *